(12) United States Patent
Allen et al.

(10) Patent No.: US 6,492,645 B1
(45) Date of Patent: Dec. 10, 2002

(54) SYSTEM FOR, AND METHOD OF, IRRADIATING ARTICLES TO STERILIZE THE ARTICLES

(75) Inventors: John Thomas Allen, San Diego; Gary K. Loda, Pleasanton; Russell Parker; George M. Sullivan, both of San Diego; Colin Brian Williams, La Jolla, all of CA (US)

(73) Assignee: Surebeam Corporation, San Diego, CA (US)

( * ) Notice: Subject to any disclaimer, the term of this patent is extended or adjusted under 35 U.S.C. 154(b) by 0 days.

(21) Appl. No.: 09/456,061

(22) Filed: Dec. 7, 1999

Related U.S. Application Data
(60) Provisional application No. 60/141,781, filed on Jun. 30, 1999.

(51) Int. Cl.[7] .................................. G21K 5/10
(52) U.S. Cl. ......................... 250/453.11; 250/455.11; 250/492.3; 378/69
(58) Field of Search ........................ 250/455.11, 453.11, 250/492.1, 492.3; 378/69

(56) References Cited

U.S. PATENT DOCUMENTS

| | | | |
|---|---|---|---|
| 4,852,138 A | * 7/1989 | Bergeret et al. | 250/453.11 |
| 5,396,074 A | * 3/1995 | Peck et al. | 250/453.11 |
| 5,995,646 A | * 11/1999 | Yonezawa et al. | 209/939 |
| 6,177,677 B1 | * 1/2001 | Alboresi et al. | 250/453.11 |

* cited by examiner

*Primary Examiner*—Jack Berman
(74) *Attorney, Agent, or Firm*—Ellsworth R. Roston; Fulwider Patton, et al.

(57) ABSTRACT

A first robotic assembly transfers articles from carriers on a transport mechanism at a loading area to a first load conveyor. The conveyor transfers the articles to a process conveyor which moves the articles through a target region at a substantially constant speed. The process conveyor then transfers the articles to a second load conveyor. A second robotic assembly then transfers the articles to article carriers on the transport mechanism at an unloading area. The load and process conveyors may be divided into two tracks. First and second radiation sources respectively disposed at first and second gaps in the process conveyor in the target region respectively irradiate the articles in both tracks in opposite directions from positions above and below the articles. Articles on the tracks may be (a) diverged on the first load conveyor to separate the articles from the dividers, (b) converged on the process conveyor to minimize the width of the radiation sources and (c) diverged on the second load conveyor. If one of the radiation sources is not operative, the other source may irradiate the opposite sides of the articles during article movements sequentially on the first tracks of the first load conveyor, the process conveyor and the second load conveyor and then sequentially on the second tracks of the first load conveyor, the process conveyor and the second load conveyor. The articles are inverted during their transfer from the first track of the second load conveyor to the second track of the first load conveyor.

71 Claims, 7 Drawing Sheets

SYSTEM FOR, AND METHOD OF, IRRADIATING ARTICLES TO STERILIZE THE ARTICLES

This application is a non-provisional application of a provisional application No. 60/141,781 filed in the United States Patent and Trademark Office on Jun. 30, 1999, for APPARATUS FOR, AND METHODS OF, STERILIZING PRODUCTS, PRIMARILY FOOD PRODUCTS in the names of John Thomas Allen, Gary K. Loda, George M. Sullivan and Colin Brian Williams as joint inventors.

This invention relates to systems for, and methods of, irradiating articles, and particularly food articles, to sterilize the articles.

BACKGROUND OF THE PREFERRED EMBODIMENTS

It has been known for some time that drugs and medical instruments and implements have to be sterilized so that they will not cause patients to become ill from harmful bacteria when they are applied to the patients. Systems have accordingly been provided for sterilizing drugs and medical instruments and implements. The drugs and the medical instruments and implements are then stored in sterilized packages until they are ready to be used.

In recent years, it has been discovered that foods can carry harmful bacteria if they are not processed properly or, even if they are processed properly, that the foods can harbor such harmful bacteria if they are not stored properly or retained under proper environmental conditions such as temperature. Some of these harmful bacteria can even be deadly.

For example, harmful bacteria have been discovered in recent years in hamburgers sold by one of the large national hamburger chains. Such harmful bacteria caused a number of purchasers of hamburgers from stores in the chain to become sick. As a result of this incident and several other similar incidents, it is now recommended that hamburgers should be cooked to a medium state rather than to a medium rare or rare state.

Similarly, harmful bacteria have been found to exist in many chickens that are sold to the public. In view of a number of incidents which have occurred, it is now recommended that all chickens be cooked so that no blood is visible in the cooked chickens.

To prevent incidents such as discussed in the previous paragraphs from occurring, various industries have now started to plan for sterilizing foods before the foods are sold to the public. This is true, for example, of hamburgers and chickens. It is also true of fruits, particularly fruits which are imported from foreign countries.

BRIEF DESCRIPTION OF THE PREFERRED EMBODIMENTS

The preferred embodiments may be used to sterilize different products including drugs and medical instruments and medical implements but are particularly adapted to be used for sterilizing foods. In sterilizing foods, it is important that the sterilization is sufficiently strong to kill harmful bacteria in the food but is not so strong as to kill beneficial bacteria in the foods.

In the preferred embodiments, a first robotic assembly transfers articles form carriers on a transport mechanism at a loading area to a first load conveyor. The conveyor transfers the articles to a process conveyor which moves the articles through a target region at a substantially constant speed. The load and process conveyors may be divided into two tracks. First and second radiation sources respectively disposed at first and second gaps on the process conveyor in the target region respectively irradiate the articles in opposite directions from positions above and below the articles. The process conveyor then transfers the articles to a second load conveyor. A second robotic assembly then transfers the articles to article carriers on the transport mechanism at an unloading area.

Articles on the tracks may be (a) diverged on the first load conveyor to separate the articles from the dividers, (b) converged on the process conveyor to minimize the width of the radiation sources and (c) diverged on the second load conveyor.

If one of the radiation sources is not operative, the other source may irradiate the opposite sides of the articles during article movements sequentially on the first tracks of the first load conveyor, the process conveyor and the second load conveyor and then sequentially on the second tracks of the first load conveyor, the process conveyor and the second load conveyor. The articles are inverted during their transfer from the first track of the second load conveyor to the second track of the first load conveyor.

BRIEF DESCRIPTION OF THE PREFERRED DRAWINGS

Figure 10:
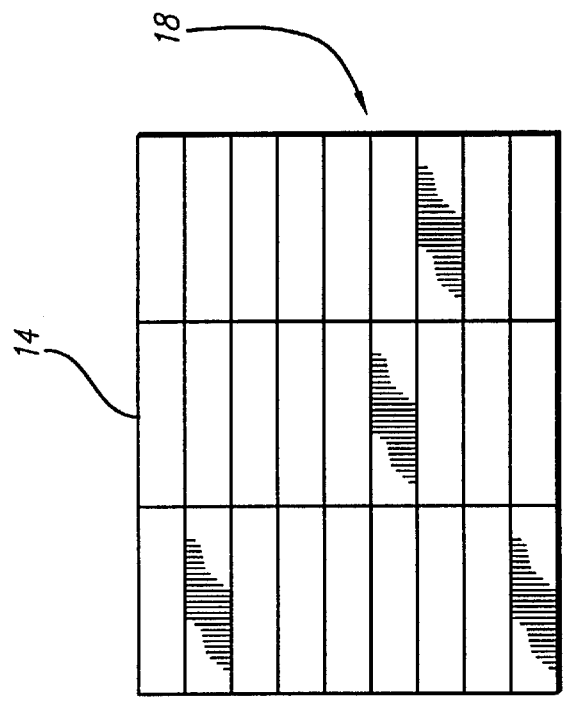
Figure 11:
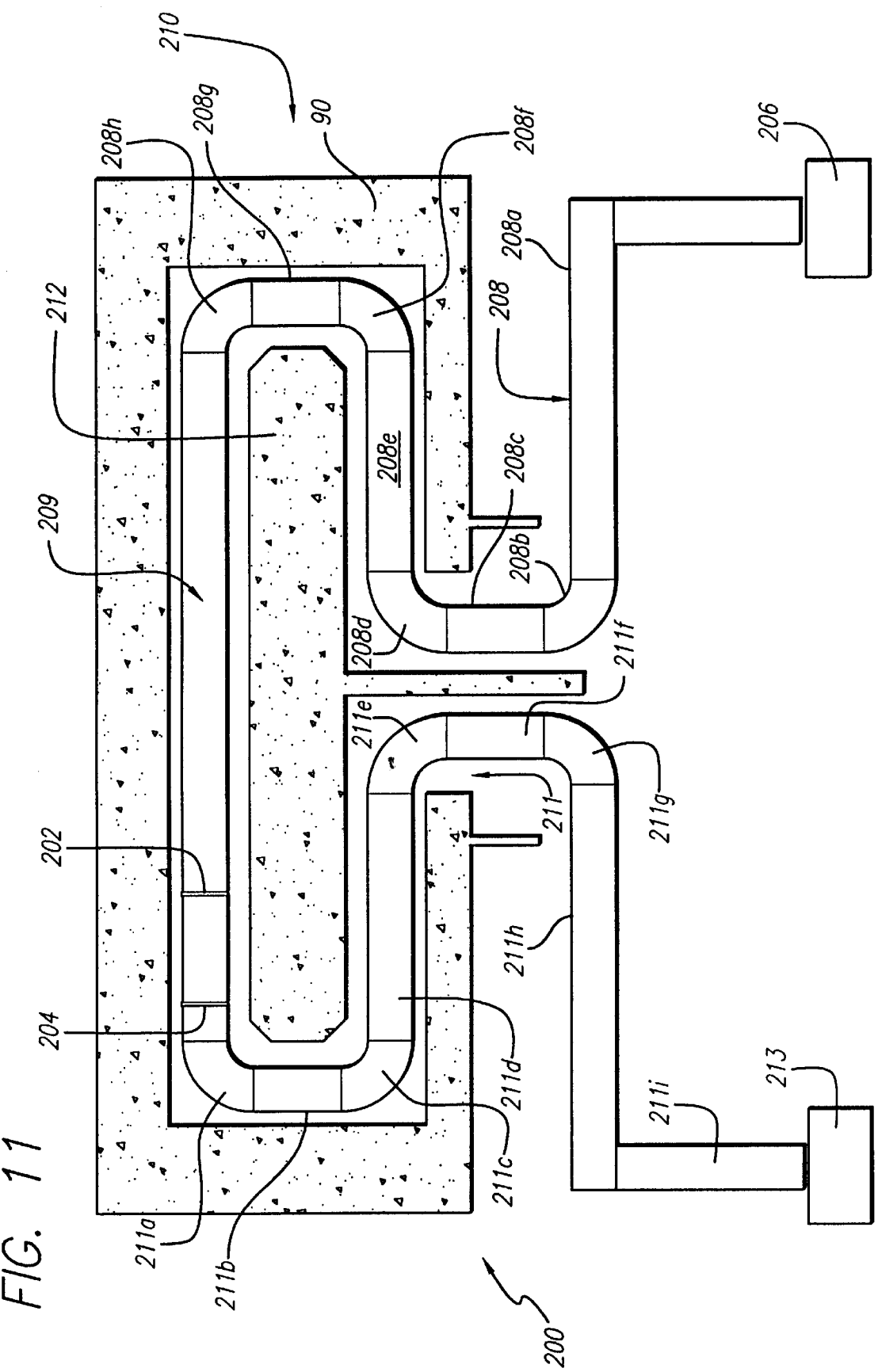

FIG. 10 is an enlarged perspective view of a plurality of articles stacked in a uniform relationship on an article carrier movable on the transport mechanism toward the loading area; and FIG. 11 is a schematic top plan view of a system constituting another preferred embodiment of the invention for irradiating opposite sides of an article, and particularly food, with electron beams to sterilize the article.

DETAILED DESCRIPTION OF PREFERRED EMBODIMENTS

The preferred embodiments incorporate a number of the features disclosed in provisional application No. 60/141,781 filed in the United States Patent and Trademark Office (USPTO) on Jun. 30, 1999. The preferred embodiments also incorporate a number of the features disclosed and claimed in U.S. Pat. No. 5,396,074 issued to Richard O. Peck, Gary M. Pageau, Colin B. Williams, John T. Allen, Bernard G. Wickersham, Leonard C. Bisgrove and Bruce D. Sellers on Mar. 7, 1995, for an IRRADIATION SYSTEM UTILIZING CONVEYOR-TRANSPORTED CARRIERS and assigned of record to the assignee of record of this application. The preferred embodiments further incorporate features disclosed and claimed in U.S. application Ser. No. 08/854,202 (docket TITAN-49534) filed on May 9, 1997, in the USPTO in the names of John T. Allen, George M. Sullivan, Michael S. Brazell, Harold B. Knowles, Anthony A. Zante, Richard J. Mendonsa, Richard C. Miller and Kenneth Whitman for ARTICLE IRRADIATION SYSTEM IN WHICH ARTICLE-TRANSPORTING CONVEYOR IS CLOSELY ENCOMPASSED BY SHIELDING MATERIAL and assigned of record to the assignee of record of this application. In addition, the preferred embodiments incorporate features disclosed and claimed in U.S. application Ser. No. 09/102,942 (docket TITAN-49641) filed in the USPTO on Jun. 23, 1998, for ARTICLE IRRADIATION SYSTEM HAVING INTERMEDIATE WALL OF RADIATION SHIELDING MATERIAL WITHIN LOOP OF CONVEYOR SYSTEM THAT TRANSPORTS THE ARTICLES in the names of John T. Allen, George M. Sullivan and Colin B. Williams as joint inventors and assigned of record to the assignee of record of this application. Reference may be made to U.S. Pat. No. 5,396,074 and/or to any or all of the pending applications specified above to complete the disclosure in this application if the disclosure in this application is found inadequate in any respect.

A preferred embodiment of a system of the invention is generally indicated at 10. The system 10 includes a loading area, generally indicated at 12 (FIG. 1), for receiving articles 14 which are disposed in a stacked relationship in article carriers 16. The articles may illustratively be drugs, drug instruments and/or drug implements. The articles may also illustratively and preferably be meats of various cuts such as hamburgers or may be chickens or fruits or juices or any of a wide variety of other foods. The articles 14 may actually be anything which harbors bacteria that are harmful to humans or animals and that will be destroyed when subjected to irradiation by the system 10. In this way, the system 10 of this invention sterilizes the articles 14 for human or animal use or consumption.

Figure 9:
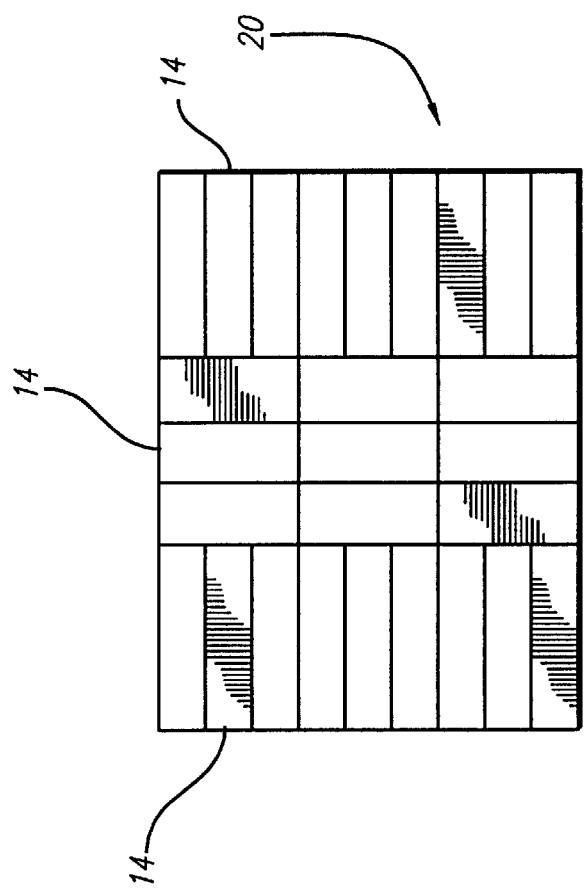
FIG. 9 is an enlarged perspective view of a plurality of articles stacked in a non-uniform relationship on an article carrier movable on a transport mechanism toward the loading area.

The articles may be disposed in the article carriers 16 in a uniformly or non-uniformly stacked relationship. A uniformly stacked relationship of the articles 14 in one of the article carriers 16 is generally illustrated at 18 in FIG. 10. A non-uniformly stacked relationship of the articles 14 in another one of the article carriers 16 is illustrated at 20 in FIG. 9. It will be appreciated that FIGS. 9 and 10 are only illustrative arrangements of the articles 14 in uniformly non-stacked and uniformly stacked relationships.

The article carriers 16 are transported on a transport mechanism generally indicated at 22, past the loading area 12. The direction of movement of the transport mechanism 22 is to the left in FIG. 1 as indicated by an arrow 24. The articles 14 are removed from the article carriers 16 by a robotic assembly 26, generally indicated at 26, which may constitute a Pallet Cell 100/200 apparatus manufactured and sold by FANUC Robotics North America, Inc.

The transfer of the articles 14 from the article carriers 16 by the robotic assembly 26 may be controlled by a controller 28. The controller 28 is programmed to consider the disposition of the individual ones of the articles 14 in the stacked relationship of the articles in the article carriers 16 on the transport mechanism 22 and to operate the robotic assembly 26 in accordance with this stacked relationship whether the stacked relationship be uniform (FIG. 10) or non-uniform (FIG. 9).

When the articles 14 are stacked in a uniform relationship (FIG. 10) in the article carriers 16, the controller 28 causes the robotic assembly 26 to move each of the successive articles 14 in the article carriers 16 in the same path to a load conveyor 30 in the loading area 12 so that each of the articles will have a particular disposition on the loading conveyor. However, when the articles 14 are stacked in the article carriers 16 in a non-uniform relationship (FIG. 9), the controller 28 causes the robotic assembly 26 to move in a path which is adjusted to take account of the non-uniform relationship so that the articles will have the particular disposition on the load conveyor 30.

The load conveyor 30 may transport the articles 14 at a selective speed such as approximately sixty feet per minute (60'/min) to approximately ninety feet per minute (90'/min). The speed of movement of the articles on the load conveyor 30 does not have to be regulated. The load conveyor 30 may be divided into two (2) tracks 30a and 30b of substantially equal widths as by a divider 32. Articles 14 may be simultaneously disposed on each of the tracks 30a and 30b. The articles on each of the tracks 30a and 30b may be the same as, or different from, the articles on the other one of the tracks.

The movement of the articles 14 on the tracks 30a and 30b may be provided by rollers 34 which may be driven by any suitable mechanism known in the art. At the position of transfer of the articles 14 to the load conveyor 30, the rollers 34 may have a herringbone configuration as indicated at 34a. In this configuration, separate rollers 34 may be disposed in each of the tracks 30a and 30b in an angled relationship to the rollers in the other track so that the end of the rollers adjacent the divider 32 is ahead of the end of the rollers distant from the divider in the direction of movement of the articles on the tracks.

In this way, the rollers 34 with the herringbone configuration 34a tend to displace the articles 14 from positions adjacent the divider 32 to positions displaced from the divider. This is desirable to insure that the movement of the articles 14 on the load conveyor 30 will not be impeded by bumping against the divider 32. When the articles have been sufficiently displaced laterally from the divider 32, the rollers are preferably provided with a configuration 36 in which the rollers are substantially perpendicular to the divider 32 and are substantially parallel to one another.

The load conveyor 30 may be formed from a plurality of segments 36a, 36b, 36c, 36d, 36e, 36f and 36g, all of which are preferably disposed in a horizontal plane. The segments 36a, 36b, 36d and 36f may preferably constitute straight segments. The straight segments 36a, 36b and 36f may be disposed in a first direction and the straight segment 36d may be disposed in a second direction substantially perpendicular to the segments 36a, 36b and 36f. The segments 36c, 36e and 36g may constitute curved segments each having a curvature of substantially 90°. The curved segment 36c joins the straight segments 36b and 36d; the curved segment 36e joins the straight segments 36d and 36f; and the curved segment 36g is contiguous to the straight segment 36f.

A process conveyor generally indicated at 38 and having a horizontal disposition in the same plane as the load conveyor 30 is contiguous at one end to the curved segment 36g of the load conveyor 30. The process conveyor 38 is constructed to move the articles 30 at a particular speed such as in the range of approximately thirty feet per minute (30'/min) to approximately sixty feet per minute (60'/min). This speed is preferably regulated by the controller 38 so that it is maintained within particular limits. If the speed should vary from these limits, the radiation applied to the articles 14 on the process conveyor 38 may be interrupted and the operation of the process conveyor may be discontinued.

The process conveyor 38 may be divided into two (2) tracks 38a and 38b, as by a divider 40, in a manner similar to the division of the load conveyor 30 into the two (2) tracks 30a and 30b by the divider 32. The process conveyor may be provided with rollers 42 having a construction similar to the rollers 34 in the load conveyor 30. The rollers 42 at the end of the process conveyor 38 adjacent to the load conveyor segment 36g has a herringbone configuration 42a. The herringbone configuration 42a of the rollers 42 differs from the herringbone configuration 34a of the rollers 34 in that the ends of the rollers 42 distal from the divider 40 lead the end of the rollers adjacent the divider in the direction of movement of the articles 14 on the rollers. The rollers 42 accordingly operate to move the articles 14 on the tracks 38a and 36b to positions contiguous to the divider 40.

The process conveyor is preferably divided into three (3) segments 39a, 39b and 39c (FIG. 4), in the direction of movement of the articles 14 on the tracks 38a and 38b, to form a gap 44a between the segments 39a and 39b and to form a gap 44b between the segments 39b and 39c. The segments 39a, 39b and 39c may respectively have lengths of approximately three feet (3'), ten feet (10') and two feet (2'). The gaps 44a and 44 may have lengths of approximately one half of one foot (½') in the direction of movement of the articles 14 on the process conveyor 38. It will be appreciated that the articles 14 should preferably have a length greater than the lengths of the gaps 44a and 44b so that the articles will be simultaneously on the segments 39a and 39b as they traverse the gap 44a and the articles will be simultaneously on the segments 39b and 39c as they traverse the gap 44b.

A radiation source 46 (FIG. 1) may be disposed to direct radiation through the gap 44a to the articles 14 on the process conveyor 38. The radiation source 46 may be disposed in a vertical direction above the process conveyor 38 to direct light downwardly on the articles 14 on the process conveyor. Similarly, a radiation source 48 may be disposed below the process conveyor 38 to direct radiation upwardly through the gap 44b to the articles 14 on the process conveyor 38. In this way the radiation will be directed against the opposite sides of the articles 14 on the process conveyor 38. The intensities of the radiation from the sources 46 and 48 should preferably be substantially equal within particular limits.

The radiation sources 46 and 48 preferably provide an electron beam against the opposite sides of the articles 14 on the process conveyor 38. Each of the radiation source 46 and 48 preferably provides an electron beam with an intensity of approximately ten (10) Mev. However, the beam can be of any intensity to kill harmful bacteria in the articles 14 being irradiated without killing beneficial bacteria in such articles. It will be appreciated that other types of radiation sources than those providing electron beams may be satisfactory, particularly in special situations. For example, gamma rays (as from cobalt or cesium) and X-rays may be satisfactory, particularly in specific instances. However, electron beams are generally preferred since they heat the articles only through a minimal range of temperatures and since the electrons directed toward the beams are only temporary in duration. For example, the temperature increase of beef patties when irradiated with an electron beam may be approximately 2° F. This allows frozen beef patties to remain frozen during and after the irradiation of the beef patties.

Electron beam radiation has a number of advantages, particularly for irradiating food, in addition to those discussed in the previous paragraph. These additional advantages include high dose rate, the ability to turn the radiation sources instantaneously on and off, the ability to regulate the irradiated area as by beam scanning, no source replenishments, the ability to regulate the strength of the radiation and the ability to operate in a dual mode (electron beam and X-ray). Other advantages of electron beam irradiation are relatively short exposure time, high power utilization in the fraction of the emitted energy usefully absorbed in the article being irradiated, simplified conveyor systems for the articles (e.g. the articles 14) because of the irradiation of individual articles rather than pallet-sized or tote-size loads and a minimization in the numbers (only 1 or 2) of passes of the articles 14 through the target region of the radiation source(s).

There are certain definite advantages to converging the articles on the tracks 38a and 38b toward the divider 40 on the process conveyor before the articles 14 reach the radiation sources 46 and 48. By converging the articles 14 toward the divider 40, the widths of the radiation from each of the radiation sources 46 and 48 are minimized. This minimizes the consumption of energy in the radiation sources 46 and 48. Alternatively, it provides for an increase in the energy directed by the radiation sources 46 and 48 against the articles 14 on the process conveyor 38.

As previously indicated, the speed of movement of the articles 14 on the load conveyor 30 is preferably greater than the speed of movement of the articles on the process conveyor 38. If the proper ratio of speeds is selected (depending on the lengths of the articles 14), the spacing between successive articles on the process conveyor is minimized, thereby increasing the efficiency in the operation of the system and decreasing the amount of power not utilized.

Figure 1:
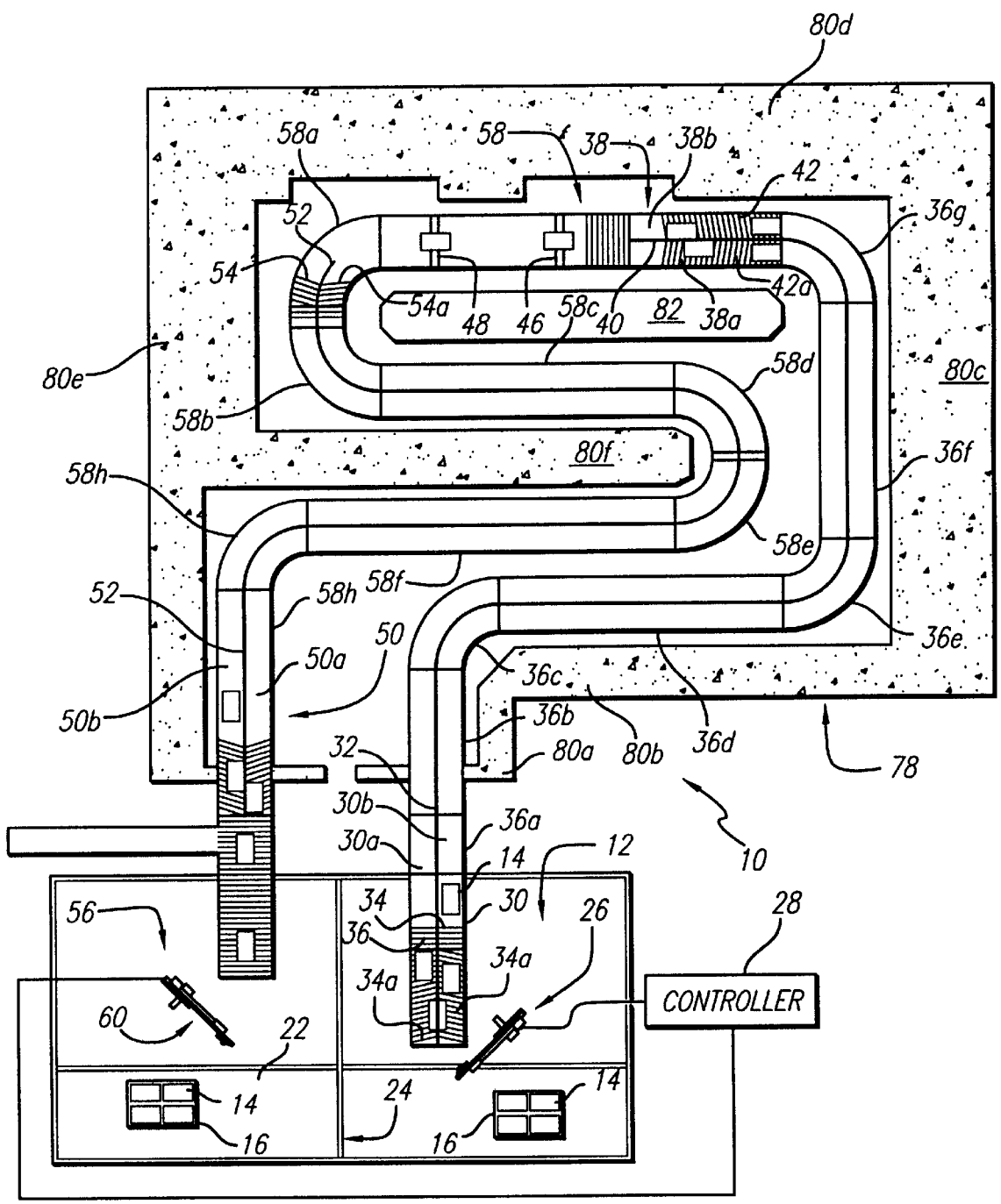
FIG. 1 is a top plan of a system constituting a preferred embodiment of the invention for irradiating opposite sides of articles, and particularly foods, with electron beams to sterilize the articles.
Figure 2:
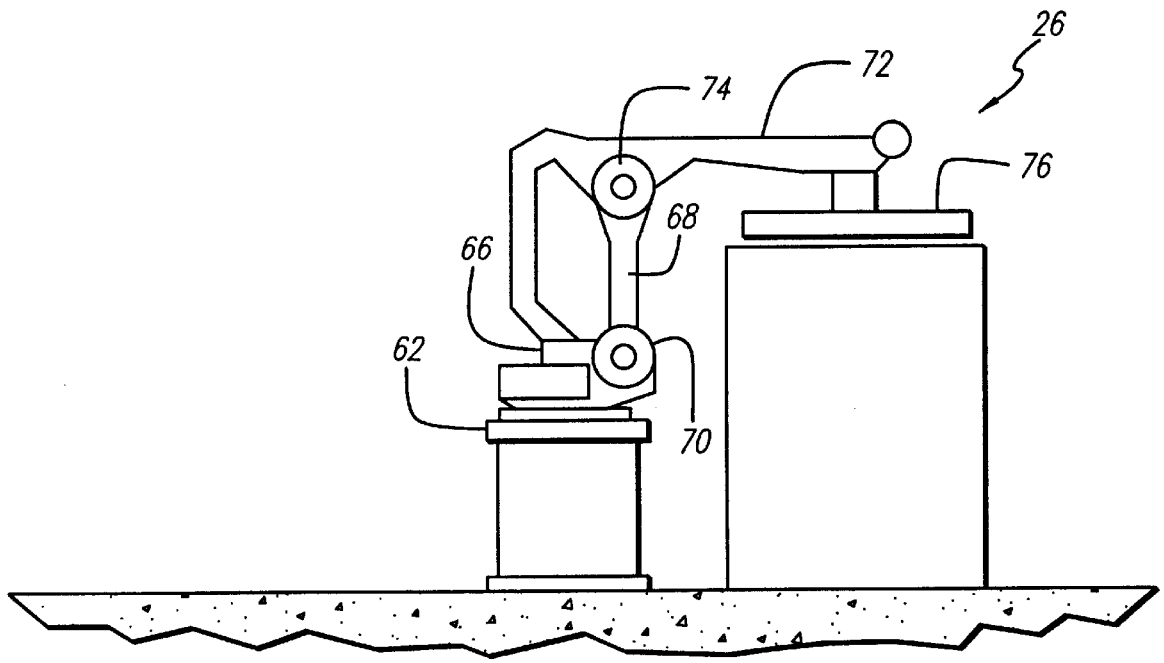
FIG. 2 is an elevational view of one of two (2) robotic assemblies included in the preferred embodiment shown in FIG. 1, one for transferring the articles form a loading area to a first load conveyor and the other for transferring articles from a second load conveyor to an unloading area.

The articles 14 on the process conveyor 38 are transferred to a load conveyor generally indicated at 50 (FIG. 1). The load conveyor 50 may have a construction similar to that of the load conveyor 30. For example, a divider 52 may be provided to divide the load conveyor 50 into two (2) tracks 50a and 50b and rollers 54 may be provided on the load conveyor to advance the articles 14 on the load conveyor toward an unloading station generally indicated at 56. The rollers 54 adjacent the process conveyor 38 may be provided with a herringbone configuration 54a similar to the herringbone configuration 34a of the rollers 34. This facilitates the movement of the articles on the load conveyor 50. The resultant separation of the articles 14 on each of the tracks 50a and 50b at the unloading station 56 facilitates the separate and individual handling of the articles at the unloading station.

The load conveyor 50 may be formed from several segments 58a, 58b, 58c, 58d, 58e, 58f, 58g and 58h. The segment 58a is contiguous to the process conveyor 30 and is curved. The segment 58b is contiguous to the segment 58c and is also curved. However, the segments 58a and 58b have opposite curvatures so that the articles 14 passing from the segment 58b travel in an opposite direction through the segment 58c relative to the direction in which the articles pass from the process conveyor 38 to the segment 58a. The segment 58c is a straight segment parallel to the process conveyor 38. The segments 58d and 58e cumulatively provide a curvature of 180° in a manner corresponding to the segments 58a and 58b. The segment 58f is straight and is parallel to the segment 58c but extends in a direction opposite to the direction of the segment 58c. The segment 58g provides a curvature of 90° between the segments 58f and 58h. The segment 58h extends in a direction parallel, but opposite, to the segment 36a in the load conveyor 30. The segment 58h extends to the unloading area 56.

A robotic assembly generally indicated at 60 may be disposed in the unloading area 56 to receive the articles 14 from the load conveyor 50 and to transfer the articles to the article carriers 16 on the transport mechanism 22. The article carriers 16 may constitute those from which the articles 14 have been previously transferred to the load conveyor 30 in the loading area 12. Because of this, the article carriers 16 adjacent to the unloading area 56 are empty. The articles 14 may be transferred to the load conveyor 50 in the unloading area 56 in a uniform relationship such as indicated at 18 in FIG. 10 or in any other uniform relationship or in a non-uniform relationship such as indicated at 20 in FIG. 9 or in any other non-uniform relationship. The transfer of the articles 14 from the load conveyor 50 to the article carriers 16 on the transport mechanism 22 in the uniform or non-uniform relationship may be under the control of the controller 28. The robotic assembly 60 in the unloading area 56 may correspond in construction to the robotic assembly 26 in the loading area 12.

Figure 3:
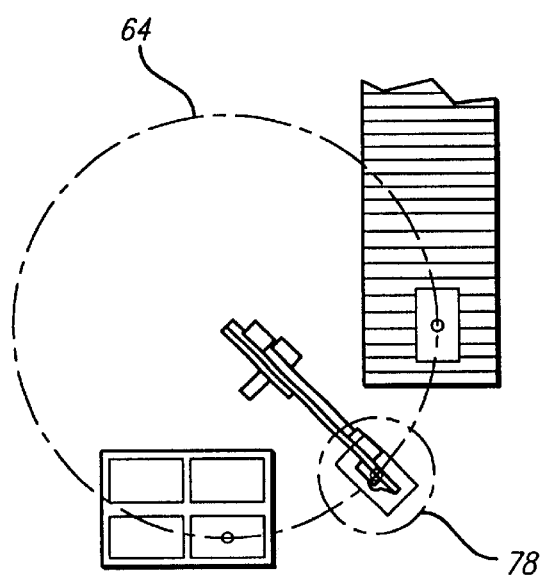
FIG. 3 is a top plan view of the robotic assembly shown in FIG. 2.
Figure 4:
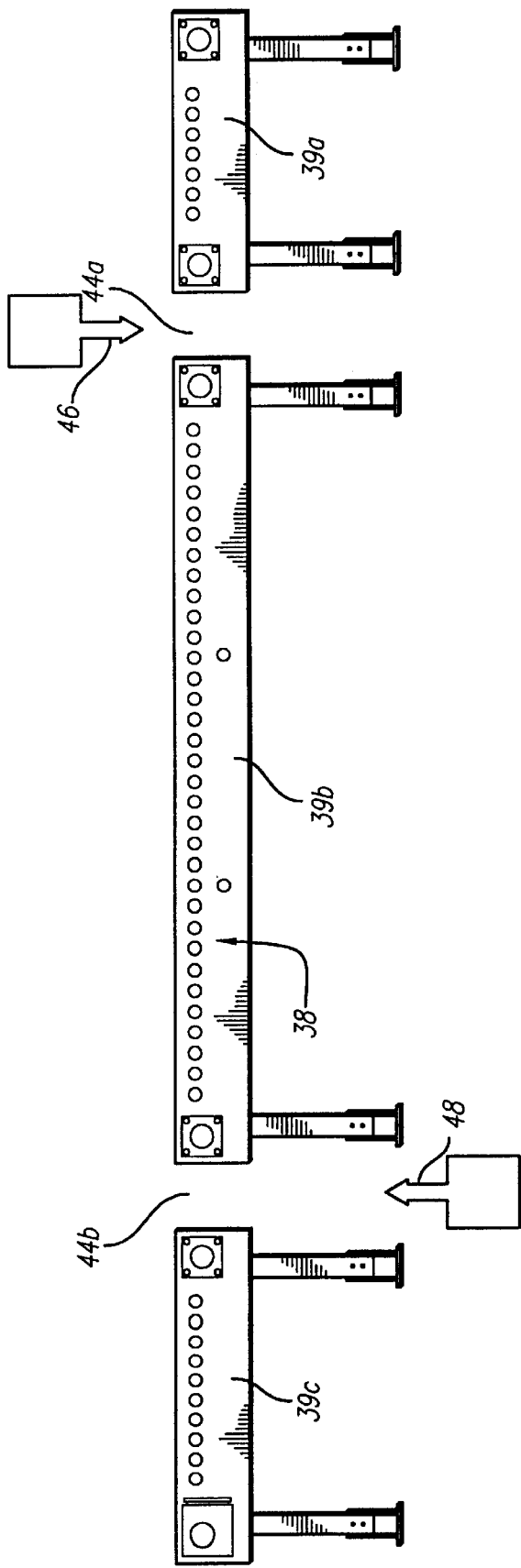
FIG. 4 is a top plan view of a process conveyor included in the preferred embodiment of the system shown in FIGS. 1–3.

The robotic assembly 26 includes a platform 62 (FIGS. 3 and 4) which is rotatable in a horizontal plane through an annulus indicated at 64 in FIG. 4. A support member 66 extends upwardly from the platform 64. An arm 68 is pivotable in a vertical plane on a pin 70 as a fulcrum, the pin being disposed on the support member 66. A strut 72 supported on the arm 68 is pivotable in a vertical plane on a pin 74. A plate 76 is supported by the strut 70 for a rotary movement in a horizontal plane through an annulus indicated at 78 in FIG. 4.

The platform 62 rotates in the horizontal plane to a position for disposition of the arm 68 in contiguous relationship to one of the articles 14 in one of the article carriers 16 on the transport mechanism 22. The arm 68 is then pivoted on the pin 70 as a fulcrum to provide for the plate 74 to lift the article 14 from the article carrier 16. The platform 62 is then rotated through a horizontal plane to the position of the load conveyor 30. The plate 76 is thereafter rotated to the position for depositing the article 14 in a properly aligned relationship on the load conveyor 30. The strut 72 is then pivoted downwardly on the pivot pin 74 as a fulcrum to deposit the article in the properly aligned relationship on the load conveyor 30.

The inclusion of the two (2) tracks in each of the load conveyor 30, the process conveyor 38 and the load conveyor 50 provides certain important advantages. It allows the articles 14 to be moved past the radiation sources 46 and 48 at one half (½) of the speed at which the articles 14 would move if only one (1) track were provided. A reduced speed is desirable because it simplifies the operation of the irradiating system 10. Another advantage of providing the two (2) tracks in each of the load conveyor 30, the process conveyor 38 and the load conveyor 50 is that one type of article 14 can be processed on one of the tracks at the same time that another type of article can be processed on the other track.

The inclusion of the radiation sources 46 and 48 to apply radiation respectively from positions above and below the articles 14 also provides certain important advantages. One advantage is that the use of the radiation sources 46 and 48 minimizes the time for processing the articles 14. Another advantage is that the thickness of the article 14 being sterilized in each pass can be increased without increasing the intensity of the radiation from the sources 46 and 48.

A further advantage is that the article 14 does not have to be inverted in order to apply radiation to the second opposite side of the article 14. Inverting the article 14 is undesirable when products such as fresh meat patties are being pasteurized. This results from the fact that blood from what was originally the bottom side of the article 14 flows to what was originally the top side of the article when the article is inverted. This blood discolors the visual appearance of the article 14 when the article is again inverted so that what was originally the top side of the article again becomes the top side of the article.

Radiation shielding generally indicated at 78 in FIG. 1 may be applied to the system 10 (a) to limit the existence of radiation from the radiation sources 46 and 48 in areas other than the target region where the articles 14 are to be irradiated and (b) to prevent radiation from the sources from reaching the loading area 12 and the unloading area 56. The radiation shielding 78 may be formed from a suitable material such as concrete. The radiation shielding 78 may encompass the system 10 and may include (a) a portion 80a adjacent the load conveyor segment 36b, (b) a portion 80b adjacent the load conveyor segments 36c, 36d and 36e, (c) a portion 80c adjacent the load conveyor segments 36e, 36f and 36g, (d) a portion 80d adjacent the load conveyor segment 36g, the process conveyor 38 and the load conveyor segment 58a, and (e) a portion 80e adjacent the load conveyor segments 58a, 58b, 58g and 58h. The radiation shielding segments 80a–80e are integral or continuous with one another. A radiation shielding portion 80f integral with the radiation shielding portions 80a–80e extends into the space between the load conveyor segments 58c and 58f.

A radiation shielding member 82 made from a suitable material such as concrete and separated from the radiation shielding portions 80a–80f is disposed in the region between the process conveyor 38 and the load conveyor segment 58c. The radiation shielding member 82 limits the amount of radiation passing to the radiation shielding portions 80a–80c and 88e and accordingly provides for a decrease in the thickness of these radiation shielding portions. The radiation shielding portions 80a 80f and the radiation shielding member 82 are preferably integral with a floor (not shown) made from a suitable material such as concrete and a roof (not shown) made from a suitable radiation shielding material such as concrete. In this way, the system 10 is disposed within an enclosure made from a radiation shielding material such as concrete.

As previously described, the articles 14 may travel on the two tracks 30a and 30b of the load conveyor 30 from the loading area 12, then on the two (2) tracks 38 and 38b of the process conveyor 38 and then on the two (2) tracks 50a and 50b of the load conveyor 50 to the unloading area 56. During the movement of the articles 14 on the process conveyor 38, each of the radiation sources 46 and 48 irradiates the articles 14 on the two tracks 38 and 38b. However, it may sometimes happen that one of the radiation sources 46 and 48 may be inoperative to irradiate the articles 14 on the tracks 38a and 38b of the process conveyor 38. Assume that it is the radiation source 46. Under such circumstances, the other one of the radiation sources 46 and 48 (assume that it is the source 48) performs a double duty and irradiates the two (2) opposite sides of the articles 14 on the tracks 38a and 38b of the process conveyor 38.

Figure 8:
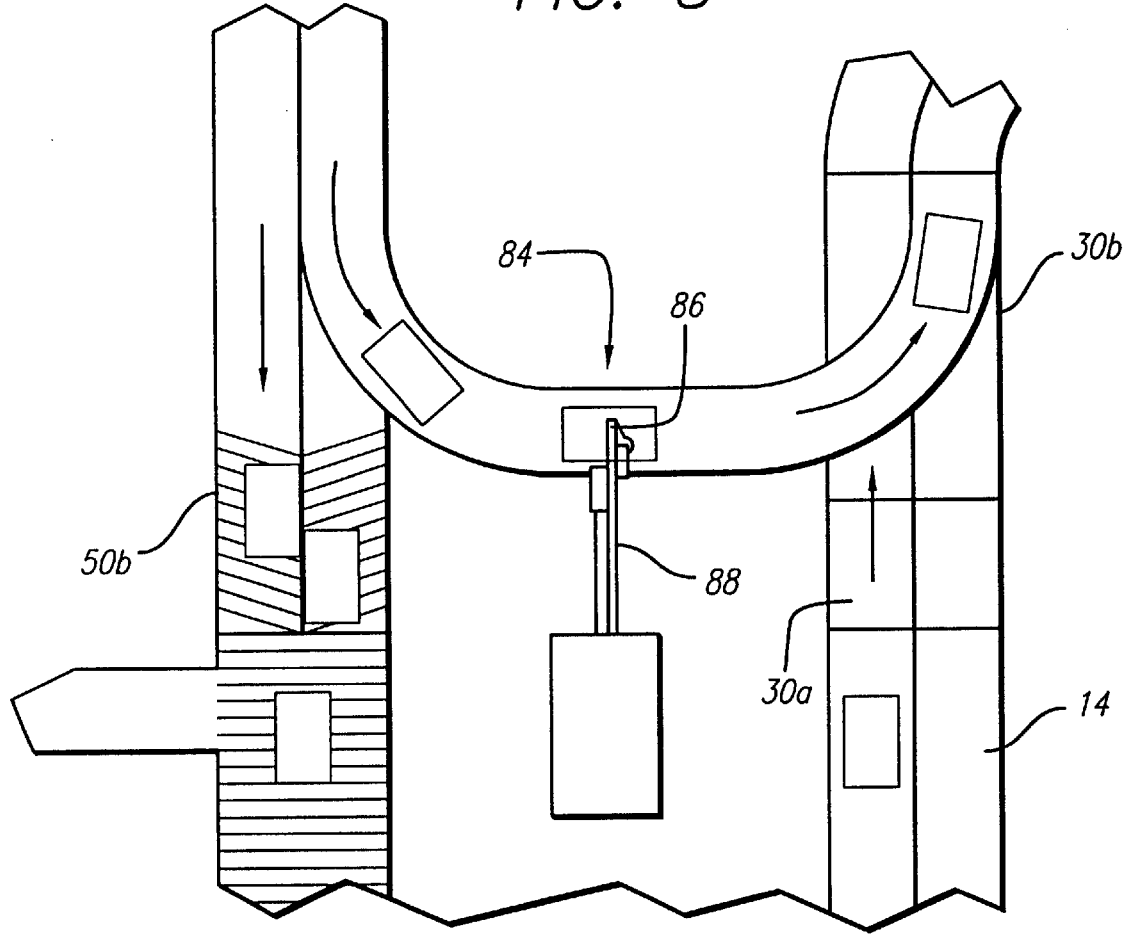
FIG. 8 is a fragmentary plan view of apparatus which may be used in conjunction with the system shown in FIGS. 1–4 for irradiating opposite sides of an article with a single radiating source when the other of the two (2) radiation sources shown in FIG. 1 becomes inoperative.

To provide for the radiation source 48 to irradiate the two (2) opposite sides of the articles 14, an alternative load conveyor (one track wide), generally indicated at 84 in FIG. 8, is provided between the first track 50a of the load conveyor 50 and the second track 30b of the load conveyor 30. The path of travel of the articles 14 is then the first track 30a of the load conveyor 30, the first track 38a of the process conveyor 38 and the first track 50a of the load conveyor 50. During this path of travel, the first side of the articles 14 is irradiated by the radiation source 48.

The articles 14 then travel from the first track 50a of the load conveyor 50 through the alternate load conveyor 84 (one track wide) to the second track 30b of the load conveyor 30. During this travel, the articles 14 reach a barrier 86. To surmount this barrier, a lifting mechanism 88 is provided to lift the articles from the side of the barrier 86 adjacent the load conveyor 50 to the side of the barrier adjacent the load conveyor 30. While the articles 14 are being lifted above the barrier 86, they are inverted. The articles 14 then travel from the second track 30b of the load conveyor 30 to the second track 38b of the process conveyor 38, then to the second track 50h of the load conveyor 50 and then to the unloading area 56. The radiation source 48 irradiates the second opposite side of the articles 14 during this second movement of the articles 14 past the radiation source 48. The same paths as described above in this paragraph and the previous paragraph are provided when the radiation 48 is unable to irradiate the articles 14 and the radiation source 46 irradiates the two (2) opposite sides of the articles.

Figure 5:
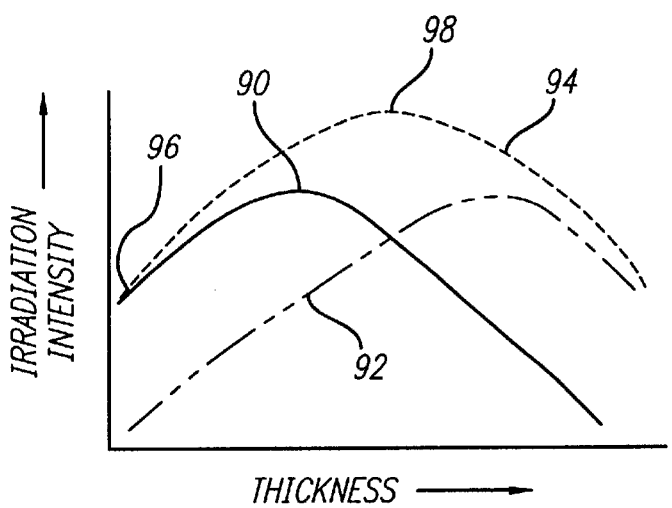
FIG. 5 shows curves illustrating the intensity of the irradiation from opposite sides of an article at progressive distances through the article and illustrating the cumulative intensity of the radiation produced in the article at the progressive distances through the article.

A curve 90 in FIG. 5 shows the irradiation intensity produced in the article 14 at different depths in the article when radiation is provided from the source 46 downwardly on the article. As will be seen, the irradiation intensity increases for some distance downwardly from the top of the article 14 until it reaches a maximum value and then the irradiation dose decreases from that maximum value with further progressive distances downwardly through the article. FIG. 5 also shows an irradiation intensity 92 produced in the article 14 by the source 48. As will be seen, the irradiation intensity from the source 48 increases for a particular distance upwardly through the article 14 from the bottom of the article to a maximum value and then decreases from that maximum value with further progressive distances upwardly through the article. The curve 92 may be considered as an inverse of the curve 90.

A curve 94 in FIG. 9 constitutes a composite of the curves 90 and 92. The composite curve 94 in FIG. 9 has a radiation intensity 96 at the top of the article 14. This corresponds substantially to the radiation intensity at the top of the article 14 for the curve 90. The intensity of the radiation in the composite curve 94 then increases from the dose 96 to a maximum value 98 at a position approximating in the article 14 the position at which the curve 90 has an irradiation intensity corresponding to the irradiation intensity in the curve 92.

Figure 6:
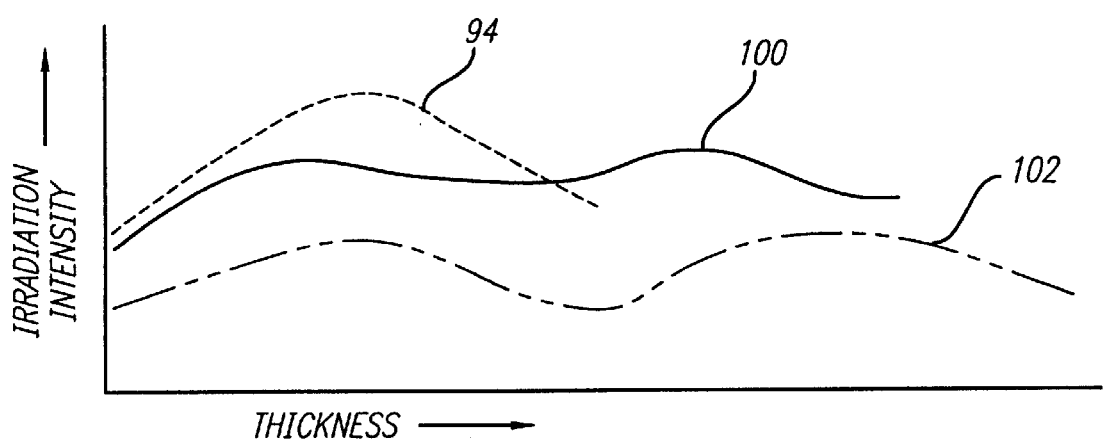
FIG. 6 shows curves illustrating the cumulative intensity of the irradiation at progressive distances through the article when the distance between the opposite sides of the article is varied.

FIG. 6 illustrates composite curves for progressive increases in the thickness of the article 14. The composite curve 94 in FIG. 5 is repeated in FIG. 6. A curve 100 in FIG. 10 constitutes a composite of the radiation intensities produced by the sources 46 and 48 when the thickness of the article 14 is increased by a first amount from the thickness of the article in the composite curve 94. A curve 102 constitutes a composite of the radiation intensities produced by the radiation sources 46 and 48 when the thickness of the article 14 is increased by a second amount greater than the first amount from the thickness of the article 14 for the composite curve 94. As will be seen for each of the composite curves 100 and 102, the difference between the maximum and minimum radiation intensities increases as the thickness of the article 14 increases above the thickness of the article for the composite curve 94.

Figure 7:
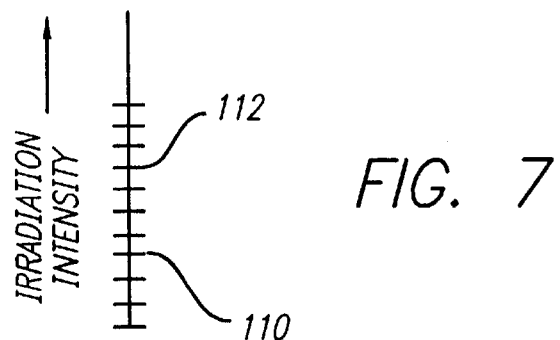
FIG. 7 is a chart showing the minimum and maximum irradiation intensities which are to be produced in the articles at the different positions in the articles.

FIG. 7 is a chart showing the range of irradiation intensities that the system described above should produce. For example, the irradiation system 10 should produce at least a first irradiation dose 110 in FIG. 7 at every position in the article 14 in order to reduce the number of harmful organisms such as E-Coli, listeria and salmonella when the article is a beef patty. If the irradiation intensity at any position in the article 14 is below the value 110, the harmful organisms (e.g. E-Coli) in the article may not be reduced sufficiently so that a person eating the beef patty can become sick. The radiation intensity should not exceed a second value 112 at every position in the article in order to preserve the life of beneficial organisms in such articles 14 as beef patties. As will be seen, the radiation intensity 112 is greater than the radiation intensity 110.

As will be seen, the difference between the maximum radiation intensity 112 and the minimum radiation intensity 110 at different vertical positions in the article 14 increases with increases in the thickness of the article. It is desirable to maintain this difference within particular limits. On the other hand, it is desirable to maintain the ability of the system 10 to process as thick articles 14 as possible in order to maintain the versatility of the system. Success is accordingly achieved by providing an optimum thickness of the articles 14 at an optimum ratio of the maximum value 112 and the minimum value 110 of the radiation dose throughout the article and by providing these parameters at the lowest cost.

FIG. 11 illustrates another preferred embodiment, generally indicated at 200, of a system constituting the invention. However, the system 200 is not as preferred as the system 10. The preferred embodiment 200 shown in FIG. 11 includes a pair of radiation sources 202 and 204 respectively corresponding to the radiation sources 46 and 48 in the embodiment shown in FIGS. 1–4 and described above. The system 200 includes a load conveyor, generally indicated at 208, having a straight portion 208a extending from a loading area 206, a portion 208b having a curvature of substantially 90°, a straight portion 208c extending in a direction opposite to the straight portion 208a, a portion 208d having a curvature of substantially 90° and extending in a direction opposite to the curved portion 208b, a straight portion 208e extending in a direction corresponding to the straight portion 208a, a portion 208f having a curvature of substantially 90°, a straight portion 208g extending in the same direction as the straight portion 208c and a portion 208h having a curvature of substantially 90°.

A process conveyor generally indicated at 209 extends from the load conveyor portion 208h in a straight path having a direction corresponding to the load conveyor portion 208a. The radiation sources 202 and 204 are disposed at gaps in the process conveyor 209. A load conveyor generally indicated at 211 extends from the process conveyor 209. The load conveyor 211 has a curved portion 211a, a straight portion 211b, a curved portion 211c, a straight portion 211d, a curved portion 211e, a straight portion 211f, a curved portion 211g and straight portions 211h and 211i. A curved portion may be disposed between the straight portions 211 h and 211i. An unloading area 213 may be disposed at the end of the straight portion 211i.

Radiation shielding material, generally indicated at 210, such as concrete envelopes the system 200 to define a chamber. Radiation shielding material 212 such as concrete is disposed within the loop defined by the process conveyor 209, the load conveyor portions 208e–208h and the load conveyor portions 211a–211e to define a wall. A wall 214 made from the radiation shielding material such as concrete extends integrally from the radiation shielding material 212 into the space between the curved portions 208d and 211e. A roof and a floor made from a radiation shielding material such as concrete may also be provided in the embodiment shown in FIG. 11.

The embodiment shown in FIG. 11 appears to have certain disadvantages relative to the embodiment shown in FIGS. 1–4 and described above. It appears to occupy more space than the embodiment shown in FIGS. 1–4. It also appears to require more radiation shielding material than the embodiment shown in FIGS. 1–4. Furthermore, the loading and unloading areas in the embodiment shown in FIG. 11 appear to be significantly removed from each other relative to the positioning of the loading area 12 and the unloading area 56 in the embodiment shown in FIGS. 1–4. This increases the difficulty of transferring the articles 14 between the loading 206 and the unloading area 213 in the embodiment shown in FIG. 11. In view of the above, the embodiment shown in FIGS. 1–4 and described above appears to be the preferred embodiment in comparison to the embodiment 200 in FIG. 11.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. A system for irradiating articles, including, at least first, second and third process conveyor segments disposed in spaced relationship to one another for moving the articles, there being a gap between the first and second process segments and a gap between the second and third process segments, each of the process conveyor segments being movable at a speed consistent with the speeds of the other process conveyor segments, a first radiation source disposed relative to the articles on the process conveyor segments, in the gap between the first and second process conveyor segments, for directing radiation in a first direction to the articles, a second radiation source disposed relative to the articles on the process conveyor segments, in the gap between the second and third process conveyor segments, for directing radiation to the articles in a second direction opposite to the first direction, the second radiation source being displaced from the first radiation source in the direction of the movement of the articles on the process conveyor segments, a loading area for the articles, the loading area being disposed before the process conveyor segments in the direction of movement of the articles on the process conveyor segments, and an unloading area for the articles, the unloading area being disposed after the process conveyor segments in the direction of movement of the articles on the process conveyor segments.

2. An irradiation system as set forth in claim 1, including, a divider in the process conveyor segments for producing two spaced and parallel tracks on the process conveyor segments, each of the tracks being constructed to transport the articles on the track separate from the articles on the other track but simultaneously with the articles on the other track.

3. A radiation source as set forth in claim 2, including, each of the tracks in each of the process conveyor segments including rollers disposed to move the articles on the track toward the articles on the other track, during the movement of the articles toward the first and second radiation sources, to obtain a disposition of the articles on the first and second tracks in substantially contiguous relationship to each other at the positions of the first and second radiation sources, each of the first and second radiation sources being provided with a width corresponding substantially to the combined widths of the articles on the two (2) spaced tracks.

4. A system as set forth in claim 3 wherein the process conveyor segments are disposed in a horizontal plane and wherein one of the radiation sources is disposed above the articles on the process conveyor segments and points downwardly toward the articles on the process conveyor segments and wherein the other of the radiation sources is disposed below the articles on the process conveyor segments and points upwardly toward the articles on the process conveyor segments.

5. A system for irradiating articles disposed in article carriers, including, a process conveyor having first, second and third segments disposed in a series relationship and separated from one another to define first and second gaps each having a length less than the width of the articles, a first load conveyor for transporting the articles and for transferring the articles to the first segment in the process conveyor, a second load conveyor for receiving the articles from the third segment in the process conveyor and for transporting the articles, a first radiation source disposed relative to the first gap for directing radiation toward the first gap in a first direction toward the articles on the process conveyor, and a second radiation source disposed relative to the second gap for directing radiation toward the second gap toward the articles on the process conveyor in a second direction opposite to the first direction.

6. A system as set forth in claim 5 wherein the cumulative radiation from the first and second sources at each position in the articles on the process conveyor is between first and second limits.

7. A system as set forth in claim 5 wherein the load conveyors and the process conveyor have dividers for producing a pair of parallel tracks each for transporting articles between the loading area and the unloading area at the same time that the other track transports articles between the loading area and the unloading area.

8. A system as set forth in claim 7, including, structure for diverging the articles on each of the tracks in the first load conveyor from the divider during the movement of the articles on the first load conveyor toward the process conveyor.

9. A system as set forth in claim 8, including, structure for converging the articles on each of the tracks toward the divider during the movement of the articles on the process conveyor toward the first radiation source.

10. A system as set forth in claim 9, including, structure for maintaining the convergence of the articles on each of the tracks on the process conveyor during the movement of the articles on the process conveyor from the first radiation source toward the second radiation source.

11. A system as set forth in claim 6, including, the load conveyors and the process conveyor having dividers for producing a pair of parallel tracks each for transporting articles between the loading area and the unloading area at the same time that the other track transports articles between the loading area and the unloading area, structure for diverging the articles on each of the tracks on the first load conveyor from the divider during the movement of the articles on the first load conveyor toward the process conveyor, structure for converging the articles on the process conveyor toward the divider during the movement of the articles on the process conveyor toward the first radiation source, and structure for maintaining the convergence of the article carriers on each of the tracks of the process conveyor during the movement of the articles on the process conveyor from the first radiation source toward the second radiation source.

12. A system for irradiating articles, including, a radiation source, a process conveyor for moving the articles past the radiation source for an irradiation of the articles by the radiation source, a load conveyor disposed relative to the process conveyor for transferring the articles to the process conveyor at a speed for movement of the articles on the process conveyor, a divider on the load conveyor for dividing the load conveyor into a pair of parallel tracks each constructed to transport individual ones of the articles at the same time as the transport of other ones of the articles on the other track, and members disposed on the tracks for converging the articles on the tracks toward one another for movement of the articles in the converged relationship on the process conveyor past the radiation source.

13. A system as set forth in claim 12 wherein the members constitute rollers rotatable in a direction to advance the articles toward the radiation source and to converge the articles during the advance of the articles toward the radiation source.

14. A system as set forth in claim 12 wherein the radiation source has a width to irradiate the articles on the tracks in the converged relationship of the articles on the tracks on the process carrier.

15. A system as set forth in claim 12 wherein the members constitute first members and wherein the first members are disposed on the process conveyor before the radiation source in the direction of movement of the articles on the tracks to converge the articles and wherein second members are disposed on the load conveyor on the tracks at a position after the movement of the articles past the radiation source for diverging the articles on each of the tracks away from the articles on the other track.

16. A system as set forth in claim 14 wherein the divider is disposed to define the tracks at the position of the diverging relationship of the articles on the tracks on the load conveyors and at the position of the converging relationship of the articles on the tracks on the process conveyor.

17. A system for irradiating articles, including, a radiation source, a process conveyor for moving the articles past the radiation source for an irradiation of the articles by the radiation source, a load conveyor disposed relative to the process conveyor for transferring the articles to the process conveyor at a speed for movement of the articles on the process conveyor, a divider on the load conveyor for dividing the load conveyor into a pair of parallel tracks each constructed to transport articles at the same time as the transport of articles on the other track, and members disposed on the tracks on the load conveyor for diverging the articles on each of the tracks on the load conveyor away from the articles on the other track on the load conveyor for movement of the articles in the diverged relationship on the load conveyor.

18. A system as set forth in claim 17 wherein the members constitute rollers rotatable in a direction to advance the articles toward the radiation source and away from the divider.

19. A system as set forth in claim 17 wherein the divider is disposed on the load conveyor to define the tracks at the position of the diverging relationship of the articles on the tracks.

20. A system for irradiating first and second opposite sides of articles, including, a radiation source, a first load conveyor divided into first and second tracks and disposed before the radiation source in the direction of movement of the articles and constructed to move the articles on the tracks, a process conveyor responsive to the movement of the articles on the first load conveyor for receiving the articles from the first load conveyor, the process conveyor being operative to move the articles past the radiation source for an irradiation of the first sides of the on the process conveyor by the radiation source, a second load conveyor divided into first and second tracks and disposed after the radiation source in the direction of the movement of the articles and constructed to receive on its first and second tracks the articles respectively disposed on the first and second tracks of the process conveyor after the irradiation of the articles on the process conveyor by the radiation source, the radiation source being constructed to initially irradiate the articles on the first track of the process conveyor and to subsequently irradiate the articles on the second track of the process conveyor, a third process conveyor coupling the first track on the second load conveyor and the second track on the first load conveyor for transferring the articles from the first track on the second load conveyor to the second track on the first load conveyor, after the irradiation by the source of the articles on the first track of the process conveyor, for movement of the articles past the radiation source a second time for irradiation of the second sides of the articles on the process conveyor by the radiation source, and a device coupled to the third load conveyor for inverting the articles transferred to the third load conveyor from the first track in the second load conveyor to obtain the irradiation of the second sides of the articles by the radiation source.

21. A system as set forth in claim 20, including, each of the first, second and third load conveyors being formed from rollers at progressive positions along the load conveyors and the first and second tracks on each of the first and second load conveyors being defined by dividers extending along the load conveyors in the direction of movement of the articles on the load conveyors.

22. A system as set forth in claim 20, including, a loading area disposed relative to the first load conveyor for providing for a transfer of the articles from the loading area to the first track on the first load conveyor, and an unloading area disposed relative to the second track on the second load conveyor for receiving the articles after the irradiation of the first and second sides of the articles by the radiation source.

23. A system as set forth in claim 19 wherein the cumulative radiation from the first and second radiation sources at each position in the articles is between first and second limits.

24. A system as set forth in claim 20, including, a loading area disposed relative to the first load conveyor for providing for a transfer of the articles from the loading area to the first track on the first load conveyor, and an unloading area disposed relative to the second track on the second load conveyor for receiving the articles after the radiation of the first and second sides of the articles by the radiation source, the cumulative radiation from the first and second radiation sources at each position in the articles being between first and second limits, and the process conveyor being constructed to convey the articles on the process conveyor at a substantially constant speed past the radiation source.

25. A system for irradiating articles, including, a load conveyor divided into first and second tracks and disposed to receive individual ones of the articles on the first track and simultaneously to receive others of the articles on the second track, a process conveyor disposed relative to the first load conveyor for receiving the articles from the first and second tracks on the first load conveyor and having first and second tracks and constructed to receive on the first and second tracks the articles respectively from the first and second tracks on the first load conveyor, the process conveyor being constructed to move the articles on the process conveyor at a particular speed and being provided with first and second gaps spaced from each other in the direction of movement of the articles on the process conveyor, a first radiation source disposed at the first gap for directing radiation toward the first gap and through the articles on the process conveyor in a first direction transverse to the direction of movement of the articles on the process conveyor and through a width encompassing the articles on the first and second tracks of the process conveyor, and a second radiation source disposed at the second gap for directing radiation toward the second gap and through the articles in a second direction opposite to the first direction and through a width encompassing the articles on the first and second tracks of the process conveyor.

26. A system as set forth in claim 25, including, a loading area disposed relative to the load conveyor for providing for a transfer of the articles from the loading area to the first and second tracks of the load conveyor, the load conveyor constituting a first load conveyor, a second load conveyor having first and second tracks for respectively receiving the articles from the first and second tracks of the process conveyor after the irradiation of the articles on the first and second tracks of the process carrier by the first and second radiation sources, and unloading area for receiving the article carriers on the first and second tracks of the second load conveyor.

27. A system as set forth in claim 25, including, the articles having first and second opposite sides, a third load conveyor having a track extending from the first track of the second load conveyor to the second track of the first load conveyor, an inverter on the third load conveyor for inverting the article carriers on the third load conveyor, and a controller responsive to a failure of one of the first and second radiation sources for activating the third load conveyor to receive the article carriers on the first track of the second load conveyor and for activating the inverter to provide for an inversion of the articles on the third load conveyor and for transferring the inverted articles to the second track on the first load conveyor for an irradiation of the second side of the articles by the one of the first and second radiation sources.

28. A system as set forth in claim 25, including, the articles having first and second opposite sides, and the controller being associated with the first and second load conveyors for providing for an irradiation of the second sides of the articles by one of the first and second radiation sources, after the irradiation of the first sides of the articles by the one of the radiation sources, when the other one of the radiation sources is unable to provide such irradiation of the second sides of the articles.

29. A system as set forth in claim 27 wherein the controller provides for an inversion of the articles after the irradiation of the first sides of the articles by the one of the radiation sources and provides for another movement of the articles past the one of the radiation sources after the inversion of the articles to obtain an irradiation of the second sides of the articles by the one of the radiation sources.

30. A system for irradiating articles disposed on article carriers, including, a first load conveyor, a transport mechanism for advancing the article carriers, a first robotic device for removing the articles individually from the article carriers on the transport mechanism and for transferring the articles to the first load conveyor, a source of radiation, a process conveyor for receiving the articles from the first load conveyor and for moving the articles past the radiation source at a substantially constant speed for an irradiation of the articles by the radiation source, a second load conveyor for receiving the irradiated articles from the process conveyor and for moving the irradiated articles toward the article carriers on the transport mechanism, and a second robotic device for removing the irradiated articles individually from the second load conveyor and for transferring the irradiated articles to the article carriers on the transport mechanism, the articles having first and second opposite sides, the source of radiation constituting a first source of radiation, a second source of radiation, there being first and second gaps in the process conveyor, the first source of radiation being disposed at the first gap in the process conveyor to direct the radiation in a first direction toward the first side of the articles, the second source of radiation being disposed at the second gap in the process conveyor to direct the radiation toward the second side of the articles in a second direction opposite to the first direction.

31. A system as set forth in claim 31 wherein apparatus is provided for obtaining a radiation of the first and second opposite sides of the articles on the process conveyor by one of the first and second sources of radiation when the other one of the sources of radiation is unable to irradiate the articles on the process conveyor.

32. A system as set forth in claim 30, including, each of the load conveyors and the process conveyor including first and second tracks each constructed to transport articles at the same time as the transport of articles by the other track, a third load conveyor coupling the first track on the second load conveyor and the second track on the first load conveyor to obtain a transfer of articles from the first track on the second load conveyor to the second track on the first load conveyor after the irradiation of the first side of the articles on the first track of the first load conveyor by one of the sources of radiation when the other one of the sources of radiation fails to irradiate the second side of the articles, and an inverter for inverting the articles during the transfer of the articles from the first track of the second load converter to the second track of the first load converter, the articles being irradiated on the second side of the articles upon the movement of the articles on the second track of the first load conveyor and the transfer of the articles to the process conveyor for movement past the radiation source.

33. A system as set forth in claim 30 wherein the source of radiation irradiates the articles on the process conveyor at every position in the articles with a strength between first and second limits.

34. A method of irradiating articles disposed on article carriers, including the steps of:

moving the article carriers on a transport mechanism, transferring articles in sequence from the article carriers to a first load conveyor during the movement of the article carriers on the transport mechanism, moving the articles on the first load conveyor to a process conveyor, moving the articles at a substantially constant speed on the process conveyor past sources of radiation to irradiate opposite sides of the articles wherein there are first and second sources of radiation and wherein the first source of radiation irradiates the first opposite side of the articles on the process conveyor and the second source of radiation irradiates the second opposite side of the articles on the process conveyor, transferring the irradiated articles from the process conveyor to a second load conveyor for movement of the irradiated articles to the transport mechanism, and transferring the irradiated articles on the second load conveyor to article carriers on the transport mechanism, and wherein the articles are inverted when one of the sources of radiation fails to irradiate the articles on the process conveyor and wherein the other one of the sources of radiation irradiates the inverted articles on the process conveyor to obtain an irradiation of the second opposite side of the articles.

35. A method of irradiating articles disposed on article carriers, including the steps of:

moving the article carriers on a transport mechanism, transferring articles in sequence from the article carriers to a first load conveyor during the movement of the article carriers on the transport mechanism, moving the articles on the first load conveyor to a process conveyor, moving the articles at a substantially constant speed on the process conveyor past sources of radiation to irradiate opposite sides of the articles, transferring the irradiated articles from the process conveyor to a second load conveyor for movement of the irradiated articles to the transport mechanism, and transferring the irradiated articles to article carriers on the transport mechanism, the first and second load conveyors and the process conveyor are divided to form two parallel tracks and wherein the articles are simultaneously disposed on the first and second tracks of each of the first and second load conveyors and wherein the articles on the two tracks of the first load conveyor are diverged before the transfer of the articles to the process conveyor and wherein the articles on the process conveyor are converged before the irradiation of the articles by the radiation source.

36. A method of irradiating articles disposed on article carriers, including the steps of:

moving the article carriers on a transport mechanism, transferring articles in sequence from the article carriers to a first load conveyor during the movement of the article carriers on the transport mechanism, moving the articles on the first load conveyor to a process conveyor, moving the articles at a substantially constant speed on the process conveyor past sources of radiation to irradiate opposite sides of the articles, transferring the irradiated articles from the process conveyor to a second load conveyor for movement of the irradiated articles to the transport mechanism, and transferring the irradiated articles to article carriers on the transport mechanism, the articles are inverted when the one of the sources of radiation fails to irradiate the articles and wherein the other one of the sources of radiation irradiates the inverted articles to obtain an irradiation of the second side of the articles and wherein the first and second load conveyors and the process conveyor are divided to form two parallel tracks and wherein the articles are simultaneously disposed on the first and second tracks of the first and second load conveyors and wherein the articles on the two tracks of the first load conveyor are diverged and wherein the articles on the process conveyor are converged before the irradiation of the articles by the radiation sources or by the other one of the radiation sources when the one of the radiation sources fails to irradiate the articles.

37. A method of irradiating articles disposed on article carriers, including the steps of:

providing a transport mechanism for the article carriers, transferring articles in sequence to a first load conveyor from each of the successive article carriers on the transport mechanism, transporting the articles in sequence at a first speed on the first load conveyor to a process conveyor, moving the articles in sequence on the process conveyor at a substantially constant speed less than the first speed, irradiating first and second opposite sides of the articles on the process conveyor, transferring the irradiated articles to a second load conveyor, providing for the movement of the articles on the second load conveyor at a speed greater than the speed of the articles on the process conveyor, and transferring the articles on the second load conveyor to article carriers on the transport mechanism, and wherein first and second sources of radiation are respectively disposed on first and second opposite sides of the articles disposed on the process conveyor to irradiate opposite sides of the articles and wherein the first side of the articles is irradiated in a first pass of the articles past one of the radiation sources and wherein the second side of the articles is irradiated in a second pass of the articles past the one of the radiation sources when the other one of the radiation sources is not operative to irradiate the articles.

38. A method as set forth in claim 37 wherein the articles are inverted in the time between the first and second passes of the articles past the one of the radiation sources.

39. A method of irradiating articles, including the steps of:

providing at least one source of radiation, providing a loading area, displaced from the source of radiation, for holding the articles, providing an unloading area displaced from the at least one source of radiation and the loading area, providing for a transfer of the articles from the loading area to a first load conveyor, providing for a transfer of the articles from the first load conveyor to a process conveyor to obtain a movement of the articles past the at least one source of radiation for an irradiation of the articles on the process conveyor by the at least one radiation source, providing for a transfer of the articles from the process conveyor to a second load conveyor for a transport of the articles to the unloading area, providing for a division of the first and second load conveyors and the process conveyor into a pair of tracks each constructed to transport articles at the same time as the transport of articles on the other track, providing for a divergence of the articles on the first and second tracks of the first load conveyor after the transfer of the articles to the first load conveyor from the loading area, and providing for a convergence of the articles on the process conveyor before the movement of the articles on the process conveyor past the at least one radiation source.

40. A method as set forth in claim 39 wherein the process conveyor provides for a movement of the articles past the at least one source of radiation at a particular speed and wherein the process conveyor is provided in segments with a gap between each pair of successive segments and wherein the at least one source of radiation constitutes first and second sources of radiation each disposed at an individual one of the gaps in the process conveyor and wherein the first source of radiation is disposed relative to the articles on the process conveyor to irradiate the first side of the articles in a first direction and wherein the second source of radiation is disposed relative to the articles on the process chamber to irradiate the second side of the articles in a second direction opposite to the first direction.

41. A method as set forth in claim 39 wherein the at least one source of radiation constitutes first and second sources of radiation and wherein the first source of radiation irradiates the articles in a first direction through the articles from the first side of the articles and wherein the second source of radiation irradiates the articles in a second direction through the articles from the second side of the articles where the second direction is opposite to the first direction and wherein the cumulative amount of irradiation of the articles at every position in the articles by the first and second sources of radiation is between first and second particular limits.

42. A method as set forth in claim 39 wherein the first and second opposite sides of the articles constitute the tops and bottoms of the articles and wherein the first and second sources of radiation are respectively disposed above and below the articles on the process conveyor and wherein the cumulative amount of irradiation of the articles on the process conveyor at every position in the articles by the first and second sources of radiation is between first and second particular limits.

43. A method of irradiating articles disposed in a non-uniform relationship on article carriers, including the steps of:

providing a loading area, providing an unloading area displaced from the unloading area, providing a transport mechanism movable past the loading and unloading areas with the article carriers disposed on the transport mechanism, providing a process conveyor, providing a controlled transfer of each of the articles in sequence from each of the successive article carriers on the transport mechanism in a substantially uniform relationship relative to the process conveyor for each of the articles, providing a movement of the articles on the process conveyor past at least one source of radiation to obtain an irradiation of the articles on the process conveyor, and providing a transfer of the irradiated articles to the article carriers on the transport mechanism as the article carriers move on the transport mechanism past the unloading area wherein the process conveyor includes first and second tracks and wherein articles are disposed on each of the first and second tracks of the process conveyor at the same time that articles are disposed on the other one of the tracks of the process conveyor and wherein each of the first and second radiation sources radiates the articles on the first and second tracks of the process conveyor and wherein the articles are disposed on one of the tracks of the process conveyor in a first movement of the articles past one of the radiation sources when the other one of the radiation sources is not operative to irradiate the articles on the process conveyor and wherein the articles are disposed on the other one of the tracks of the process conveyor in a second movement of the articles past the one of the radiation sources when the other one of the radiation sources is not operative to irradiate the articles on the process conveyor and wherein the articles are transferred from the one of the tracks to the other one of the tracks and are inverted between the times of the first and second movements of the articles past the one of the radiation sources.

44. A method of irradiating articles including the steps of:

providing a process conveyor, dividing the process conveyor into two (2) tracks, each movable at the same speed as the other track and each constructed to hold the articles to be irradiated, providing a radiation source constructed to irradiate articles, moving the process conveyor past the radiation from the radiation source to obtain an irradiation of the articles on the two tracks, and converging the articles on each of the tracks toward the divider during the movement of the process conveyor toward the radiation source to minimize the width of the radiation from the radiation source.

45. A method as set forth in claim 44, including the steps of:

providing a load conveyor for conveying the articles toward the process conveyor and dividing the load conveyor into two (2) tracks corresponding to the two (2) tracks on the process conveyor, transferring the articles from the load conveyor to the process conveyor for the movement of the articles by the process conveyor toward the radiation source, diverging the articles on the two (2) tracks on the load conveyor during the movement of the articles on the load conveyor toward the process conveyor, and transferring the articles from a loading area to the load conveyor for movement of the articles to the process conveyor.

46. A method as set forth in claim 44 including the steps of:

providing a load conveyor for conveying the articles from the process conveyor after the irradiation of the articles by the radiation source, dividing the load conveyor into two (2) tracks corresponding to the two (2) tracks on the process conveyor, transferring the articles on the two (2) tracks on the process conveyor to the two (2) tracks on the load conveyor after the irradiation of the articles on the process conveyor, diverging the articles from the divider during the movement of the articles on the load conveyor, and transferring the articles from the level conveyor to an unloading area.

47. A method as set forth in claim 46 wherein the process conveyor conveys the articles at a substantially constant speed past the radiation from the radiation source and wherein the load conveyors convey the articles at a different speed than the speed at which the articles are conveyed on the process conveyor.

48. A method as set forth in claim 44 wherein the process conveyor is formed from three (3) segments disposed in a series relationship and wherein the second segment is separated by gaps from the first and third segments and wherein the gaps have a length less than the length of the articles and wherein first and second radiation sources are respectively disposed in the gaps separating the second segment from the first and third segments and wherein the first and second radiation sources are disposed on the opposite sides of the process conveyor and wherein the first radiation source is pointed toward the article on the process conveyor in a direction opposite to the direction in which the second radiation source is pointed.

49. A method as set forth in claim 45 wherein the articles are disposed in a non-uniform relationship to one another on the load conveyor and are transferred to the process conveyor for disposition on the process conveyor in a substantially uniform relationship to one another.

50. A method as set forth claim 45 wherein rollers are provided on the process conveyor to converge the articles on the first and second tracks on the process conveyor toward the divider and wherein rollers are provided in the load conveyor to diverge the articles on the load conveyor from the divider on the load conveyor.

51. A method as set forth in claim 48, including the steps of:
providing for one of the radiation sources to irradiate first and second opposite sides of the article when the other one of the first and second radiation sources is inoperative.

52. A method as set forth in claim 48, including the steps of:
extending a third load conveyor from the first track of the second load conveyor to the second track of the first load conveyor,
inverting the articles on the third load conveyor, and
activating the third load conveyor to receive the articles on the first track of the second load conveyor and to invert the articles and to transfer the inverted articles to the second track on the first load conveyor to obtain a radiation of the second side of the articles on the second track of the first load conveyor.

53. A system for irradiating articles, including,
a process conveyor for conveying the articles in a first direction and including a divider for separating the conveyor into first and second tracks,
a source of radiation for providing radiation in a second direction transverse to the first direction, and
structure for converging the articles in the two (2) tracks on the process conveyor toward the divider on the process conveyor during the movement of the articles on the process conveyor, thereby to limit the width of the radiation source.

54. A system as set forth in claim 53 wherein
the process conveyor is divided into three (3) segments disposed in a series relationship and wherein
the second segment is respectively separated by first and second gaps from the first and third segments and wherein
the gaps have a length less than the length of the articles and wherein
the source of radiation comprises first and second sources of radiation and wherein
the first radiation source is disposed adjacent the first gap on a first side of the article and the second radiation source is disposed adjacent the second gap on a second side of the article opposite to the first side of the articles.

55. A system as set forth in claim 53, including
a load conveyor disposed relative to the process conveyor for conveying the articles and for transferring the articles to the process conveyor,
the load conveyor including a divider for separating the load conveyor into first and second tracks each constructed to convey articles at the same time as the conveyance of articles by the other track,
the load conveyor being constructed to diverge the articles from the divider during the conveyance of the articles on the load conveyor.

56. A system as set forth in claim 53, including
a load conveyor disposed relative to the process conveyor for conveying the articles after the irradiation of the articles by the source of radiation,
the load conveyor including a divider for separating the load conveyor into first and second tracks each constructed to convey articles at the same time as the conveyance of articles by the other track,
the load conveyor being constructed to diverge the articles from the dividers during the conveyance of the articles on the load conveyor.

57. A system as set forth in claim 55, including
a loader for providing articles to the load conveyor,
the process conveyor being constructed to convey the articles on the process conveyor at a substantially constant speed,
the load conveyor and the process conveyor being disposed relative to each other and constructed to provide the conveyance of the articles on the load conveyor at a different speed than the speed of the articles on the process conveyor and to provide for a substantially uniform spacing of the articles on the process conveyor.

58. A system as set forth in claim 55 wherein
the articles are disposed in a non-uniform relationship to one another on the load conveyor and wherein
a controller is provided in association with the load conveyor and the process conveyor to transfer the articles from the load conveyor to the process conveyor in a substantially uniform relationship to one another on the process conveyor.

59. A system as set forth in claim 55 wherein
rollers are provided on the process conveyor to converge the articles on the first and second tracks on the process conveyor toward the divider and wherein
rollers are provided on the load conveyor to diverge the articles on the conveyor from the divider.

60. A system as set forth in claim 55 wherein
a second load conveyor is disposed relative to the process conveyor to receive the articles from the process conveyor after the irradiation of the articles and is provided with a divider to separate the second load conveyor into first and second tracks and wherein the articles are irradiated by a first radiation source disposed on a first side of the articles and by a second radiation source disposed on a second side of the articles opposite to the first side and wherein
the first and second load conveyors are interrelated to provide for one of the radiation sources to irradiate the two (2) opposite sides of the articles when the other one of the radiation sources is inoperative.

61. A system as set forth in claim 60, wherein
the interrelationship between the first and second load conveyors is provided by a third load conveyor to transfer the articles from the first track on the second load conveyor to the second track on the first load conveyor when the second radiation source is inoperative and wherein
an inverter is disposed relative to the third load conveyor to invert the articles on the third load conveyor, thereby providing for an irradiation of the first side of the articles by the first radiation source during the disposition of the articles on the first track of the first load conveyor and for an irradiation of the second side of the articles by the second radiation source during the disposition of the articles on the second track of the first load conveyor.

62. A system for irradiating articles, including
a source of radiation,
a process conveyor for moving the articles on the process conveyor past the source of radiation for irradiating the articles,
a divider on the process conveyor for dividing the process conveyor into first and second tracks, and members on the first and second tracks of the process conveyor for conveying the articles on the tracks toward the divider during the movement of the articles on the process conveyor toward the radiation from the source.

63. A system as set forth in claim 62 wherein the radiation source is on a first side of the process conveyor to radiate a first side of the articles and wherein
   a second radiation source is on a second side of the process conveyor to radiate a second side of the articles opposite to the first side of the articles.

64. A system as set forth in claim 63 wherein gaps are provided in the process conveyor at the positions of the radiation from the first and second sources.

65. A system as set forth in claim 62 wherein the articles are moved by the process conveyor past the source of radiation at a substantially constant speed.

66. A system as set forth in claim 63 wherein gaps are provided on the process conveyor at the positions of the radiation from the first and second sources, and the articles are moved by the process conveyor past the source of radiation at a substantially constant speed.

67. A method of irradiating articles, including the steps of:

providing a divider on a process conveyor in a longitudinal direction corresponding to a direction of movement of the process conveyor, directing radiation toward the articles on the process conveyor during the movement of the articles on the process conveyor, and converging the articles on the process conveyor during their movement on the process conveyor toward the radiation from the source.

68. A method as set forth in claim 67 wherein the process conveyor moves at a substantially constant speed past the radiation from the source.

69. A method as set forth in claim 67 wherein the source of radiation constitutes a first source of radiation and wherein
   a second source of radiation is disposed on a second side of the articles opposite to the first side of the articles and wherein
      first and second gaps are provided in the process conveyor at spaced positions in the direction of movement of the process conveyor respectively corresponding to the position of the first and second sources of radiation.

70. A method as set forth in claim 69 wherein the first and second sources of radiation are respectively disposed to pass radiation through the first and second gaps to the articles on the process conveyor and wherein
   the dimensions of the gaps in the direction of movement of the process conveyor is less than the dimension of the articles in the direction of movement of the process conveyor.

71. A method as set forth in claim 68 wherein the source of radiation constitutes a first source of radiation and wherein
   a second source of radiation is disposed on a second side of the articles opposite to the first side of the articles and wherein
      first and second gaps are provided in the process conveyor at spaced positions in the direction of movement of the process conveyor, and
   wherein the first and second sources of radiation are respectively disposed to pass radiation through the first and second gaps and wherein
      the dimensions of the gaps in the direction of movement of the process conveyor is less than the dimension of the articles in the direction of movement of the process conveyor.

\* \* \* \* \*

UNITED STATES PATENT AND TRADEMARK OFFICE
CERTIFICATE OF CORRECTION

PATENT NO.   : 6,492,645 B1
DATED        : December 10, 2002
INVENTOR(S)  : John Thomas Allen et al.

It is certified that error appears in the above-identified patent and that said Letters Patent is hereby corrected as shown below:

<u>Column 15,</u>
Lines 61 and 64, before "load conveyors". Delete "first".

<u>Column 16,</u>
Lines 8 and 12, before "article", add -- width of the --.

<u>Column 17,</u>
Line 32, change "31", to read -- 30 --.

<u>Column 18,</u>
Line 55, after "conveyors", add -- and the process conveyor --.

Signed and Sealed this

Twenty-seventh Day of May, 2003

JAMES E. ROGAN
*Director of the United States Patent and Trademark Office*